United States Patent
Ito et al.

(10) Patent No.: US 9,510,770 B2
(45) Date of Patent: Dec. 6, 2016

(54) MAGNETIC RESONANCE IMAGING APPARATUS AND SAR ESTIMATION METHOD

(75) Inventors: Kosuke Ito, Tokyo (JP); Masahiro Takizawa, Tokyo (JP)

(73) Assignee: HITACHI, LTD., Tokyo (JP)

( * ) Notice: Subject to any disclaimer, the term of this patent is extended or adjusted under 35 U.S.C. 154(b) by 1097 days.

(21) Appl. No.: 13/509,094

(22) PCT Filed: Nov. 25, 2010

(86) PCT No.: PCT/JP2010/070964
§ 371 (c)(1),
(2), (4) Date: May 10, 2012

(87) PCT Pub. No.: WO2011/065393
PCT Pub. Date: Jun. 3, 2011

(65) Prior Publication Data
US 2012/0226137 A1  Sep. 6, 2012

(30) Foreign Application Priority Data

Nov. 27, 2009 (JP) ................................. 2009-270261
Nov. 12, 2010 (JP) ................................. 2010-253339

(51) Int. Cl.
*A61B 5/055* (2006.01)
*G01R 33/28* (2006.01)

(52) U.S. Cl.
CPC ............. *A61B 5/055* (2013.01); *G01R 33/288* (2013.01)

(58) Field of Classification Search
CPC ............................. A61B 5/055; G01R 33/288
See application file for complete search history.

(56) References Cited

U.S. PATENT DOCUMENTS

| 8,698,495 B2* | 4/2014 | Nehrke ................ G01R 33/246 324/309 |
| 2006/0047198 A1* | 3/2006 | Sugimoto .............. A61B 5/055 600/410 |
| 2007/0096735 A1 | 5/2007 | Morich et al. |

FOREIGN PATENT DOCUMENTS

| JP | 8-38447 | 2/1996 |
| JP | 11-253416 | 9/1999 |
| JP | 2007-526783 | 9/2007 |
| JP | 2009-504224 | 2/2009 |
| WO | WO 2007/017779 A2 | 2/2007 |

OTHER PUBLICATIONS

International Search Report in PCT/JP2010/070964.

* cited by examiner

*Primary Examiner* — Elmer Chao
(74) *Attorney, Agent, or Firm* — Cooper & Dunham LLP

(57) ABSTRACT

In order to further improve the accuracy of SAR estimation by accurately estimating, for each object, the energy of RF pulses absorbed into a part of an object, for example, a head, on the basis of measurement performed before main imaging, a nuclear magnetic resonance imaging apparatus estimates a head SAR by calculating a signal $S_h$ generated from the head and a signal $S_b$ generated from the whole object, calculating the ratio α between the signal generated from the head and the signal generated from the whole object, and calculating the energy $E_h$ absorbed into the head using the ratio of the signals.

6 Claims, 20 Drawing Sheets

MAGNETIC RESONANCE IMAGING APPARATUS AND SAR ESTIMATION METHOD

TECHNICAL FIELD

The present invention relates to a nuclear magnetic resonance imaging (hereinafter, referred to as "MRI") apparatus which measures a nuclear magnetic resonance (hereinafter, referred to as "NMR") signal from hydrogen, phosphor, or the like in an object and images density distribution, relaxation time distribution, or the like of the atomic nucleus and in particular, to an MRI apparatus and a SAR (Specific Absorption Rate) estimation method with improved accuracy in estimating the SAR.

BACKGROUND ART

The MRI apparatus is an apparatus which measures an NMR signal generated by an object, especially, nuclear spins which form human tissue, and images the shapes or functions of the head, abdomen, limbs, and the like in a two-dimensional manner or in a three-dimensional manner. In the imaging, different phase encoding is given to NMR signals by the gradient magnetic field and frequency encoding is also given to the NMR signals, and the NMR signals are measured as time-series data. The measured NMR signals are reconstructed as an image by two-dimensional or three-dimensional Fourier transform.

The MRI apparatus needs to emit a high frequency magnetic field pulse (RF pulse) to the human body in order to generate an NMR signal. Heat is generated when the human body absorbs the RF pulse. The amount of absorption of RF pulses per unit time and unit mass is called a SAR (Specific Absorption Rate). According to IEC 60601-2-33, $2^{nd}$ edition, SARs to be controlled are whole body SAR, partial body SAR, head SAR, and local SAR, and these are defined by (Expression 1), (Expression 2), (Expression 3), and (Expression 4), respectively.

[Expression 1]

$$\text{Whole body } SAR[W/kg] = \frac{E[W]}{M[kg]} \quad \text{(Expression 1)}$$

[Expression 2]

$$\text{Partial body } SAR[W/kg] = \frac{E[W]}{m_p[kg]} \quad \text{(Expression 2)}$$

[Expression 3]

$$\text{Head } SAR[W/kg] = \frac{E_h[W]}{m_h[kg]} \quad \text{(Expression 3)}$$

Local SAR [W/kg]=energy absorbed into arbitrary 10 g per unit time [Expression 4]

Here, E indicates the amount of absorption of RF pulses per unit time, M indicates the mass of an object, $m_p$ indicates the object mass of a portion to which an RF pulse is emitted, $E_h$ indicates electric power of RF pulses absorbed into the head, and $m_h$ indicates the mass of the head. For the four types of SAR described above, upper limits are shown in NPL 1, and it is necessary to comply with them.

In the MRI apparatus, it is also necessary to increase the frequency of an RF pulse applied according to an increase in the static magnetic field strength. Electric power of absorbed RF pulses is proportional to the square of the frequency of the RF pulse. Accordingly, particularly when developing a high-magnetic-field MRI apparatus, it is very important to estimate the SAR accurately.

Regarding the estimation of the SAR, a method of calculating the amount of absorbed RF pulses is disclosed in NPL 1. In NPL 2, the amount of absorbed RF pulses is calculated by solving the Maxwell equation approximately. PTL 1 discloses a method of calculating the whole body SAR, the partial body SAR, and the head SAR accurately by changing the model of the object according to the object data, an imaging part, or an imaging parameter.

RELATED ART LITERATURES

Patent Literatures

[PTL 1] U.S. Pat. No. 6841999

Non Patent Literatures

[NPL 1] IEC60601-2-33, 2nd edition
[NPL 2] Journal of Magnetic Resonance Imaging 12:46-67 (2000) David I. Hoult, M A, D Phil: Sensitivity and Power Deposition in a High-Field Imaging Experiment
[NPL 3] Hai-King Margaret Cheng, Graham A Wright, "Rapid High-Resolution T1 Mapping by Variable Flip Angles: Accurate and Precise Measurements in the Presence of Radiofrequency Field Inhomogeneity", Magnetic Resonance in Medicine 55:566-574.

OUTLINE OF INVENTION

Problems to be Solved by the Invention

As described above, calculating the amount of absorbed RF pulses is disclosed in NPL 1 and NPL 2. However, calculating the energy of RF pulses absorbed into the head accurately is not disclosed in NPL 2. Moreover, in the method disclosed in NPL 1, calculation using a model is performed. However, there is a limit in calculating the value of the SAR for each object accurately.

It is an object of the present invention to further improve the accuracy of SAR estimation by accurately estimating, for each object, the energy of RF pulses absorbed into a part of an object, for example, a head, on the basis of measurement performed before main imaging.

Means for Solving the Problems

In order to achieve the above-described object, a nuclear magnetic resonance imaging apparatus of the present invention is formed as follows.

The present invention is a nuclear magnetic resonance imaging apparatus including: a static magnetic field generator which generates a static magnetic field in a space where an object is placed; a gradient magnetic field application section which applies a gradient magnetic field to the object; a high frequency magnetic field generator which applies an RF pulse with a magnetic resonance frequency to the object; a signal detector which detects an echo signal generated from the object; an image reconstruction section which reconstructs an image using the detected echo signal; and a controller which controls the gradient magnetic field application section, the high frequency magnetic field generator, and the signal detector, and is characterized in that the controller estimates a SAR of a part of the object by calculating a signal generated from the part of the object and a signal generated from the whole object, calculating a ratio between the signal generated from the part of the object and the signal generated from the whole object, and calculating energy absorbed into the part of the object using the ratio of the signals.

In addition, the present invention is a nuclear magnetic resonance imaging apparatus including: a static magnetic field generator which generates a static magnetic field in a space where an object is placed; a gradient magnetic field application section which applies a gradient magnetic field to the object; a high frequency magnetic field generator which applies an RF pulse with a magnetic resonance frequency to the object; a signal detector which detects an echo signal generated from the object; an image reconstruction section which reconstructs an image using the detected echo signal; and a controller which controls the gradient magnetic field application section, the high frequency magnetic field generator, and the signal detector, and is characterized in that the controller estimates a head SAR by calculating a signal generated from the head and a signal generated from the whole object, calculating a ratio between the signal generated from the head and the signal generated from the whole object, and calculating energy absorbed into the head using the ratio of the signals.

Moreover, in the present invention, the controller may acquire an FID signal and calculate a signal, which is generated from the head, and a signal, which is generated from the whole object, from the FID signal.

Moreover, in the present invention, the controller may acquire projection data in a body axis direction and calculate a signal, which is generated from the head, and a signal, which is generated from the whole object, from the projection data signal.

Moreover, in the present invention, the controller may capture a 3D image with the inside of an entire TR-body coil as an imaging field of view and calculate a signal, which is generated from the head, and a signal, which is generated from the whole object, from a pixel value of the 3D image.

Moreover, in the present invention, an image of three orthogonal cross sections having the inside of an entire TR-body coil as an imaging field of view may be acquired, and a head region may be selected using the image of the three orthogonal cross sections.

Moreover, in the present invention, a 3D image having the inside of an entire TR-body coil as an imaging field of view may be captured, and a head region may be selected using the 3D image.

Moreover, in the present invention, a position of a receiving coil for the head may be measured, and a head region may be selected using the position of the receiving coil for the head.

Moreover, in the present invention, projection data in a body axis direction may be acquired, and a head region may be selected from a minimum value of the projection data.

In addition, the present invention is a SAR estimation method in the magnetic resonance imaging apparatus.

Advantage of the Invention

By accurately estimating, for each object, the energy of RF pulses absorbed into a part of an object, for example, a head, on the basis of measurement performed before main imaging, it is possible to further improve the accuracy of SAR estimation. Therefore, since the static magnetic field strength of an MRI apparatus can be set as large as possible, a high-quality MRI image can be obtained.

MODE FOR CARRYING OUT THE INVENTION

Figure 1:
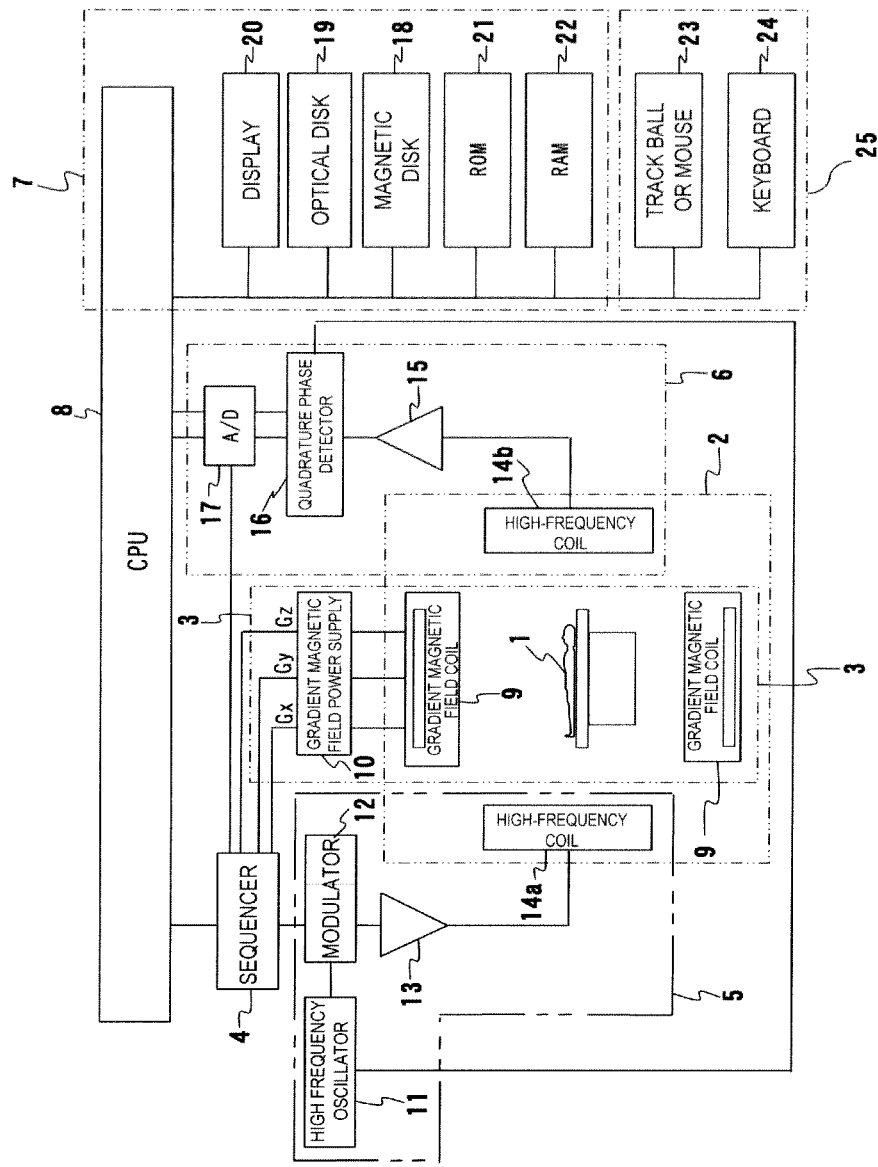
FIG. 1 is a view showing the entire configuration of an MRI apparatus related to the present invention.

Hereinafter, preferred embodiments of an MRI apparatus of the present invention will be described in detail according to the accompanying drawings. In addition, in all drawings for explaining the embodiments of the present invention, the same reference numerals are given to those with the same functions and repeated explanation thereof will be omitted.

First, the outline of an example of an MRI apparatus related to the present invention will be described on the basis of FIG. 1. FIG. 1 is a block diagram showing the entire configuration of an example of the MRI apparatus related to the present invention. This MRI apparatus acquires a tomographic image of an object using an NMR phenomenon. As shown in FIG. 1, the MRI apparatus is configured to include a static magnetic field generation system 2, a gradient magnetic field generation system 3, a signal transmission system 5, a signal receiving system 6, a signal processing system 7, a sequencer 4, and a central processing unit (CPU) 8.

The static magnetic field generation system 2 generates a uniform static magnetic field in a surrounding space of an object 1 in a direction perpendicular to the body axis in the case of a vertical magnetic field method and in the body axis direction in the case of a horizontal magnetic field method.

A permanent magnet type, normal conduction type, or superconducting type static magnetic field generator is disposed around the object 1.

The gradient magnetic field generation system 3 includes gradient magnetic field coils 9 wound in three axial directions of X, Y, and Z, which are the coordinate system (stationary coordinate system) of the MRI apparatus, and a gradient magnetic field power source 10 which drives each gradient magnetic field coil and applies gradient magnetic fields Gx, Gy, and Gz in the three axial directions of X, Y, and Z by driving the gradient magnetic field power source 10 of each coil according to a command from the sequencer 4, which will be described later. At the time of photographing, a slice-direction gradient magnetic field pulse (Gs) is applied in a direction perpendicular to the slice surface (cross section of photographing) so that a slice surface of the object 1 is set, and a phase-encoding-direction gradient magnetic field pulse (Gp) and a frequency-encoding-direction gradient magnetic field pulse (Gf) are applied in the two remaining directions, which are perpendicular to the slice surface and are also perpendicular to each other, so that the positional information in each direction is encoded in an echo signal.

The sequencer 4 is a control means for repeatedly applying a high frequency magnetic field pulse (hereinafter, referred to as an "RF pulse") and a gradient magnetic field pulse according to a predetermined pulse sequence, and operates under the control of the CPU 8 and transmits various commands, which are required to collect data of a tomographic image of the object 1, to the signal transmission system 5, the gradient magnetic field generation system 3, and the signal receiving system 6.

The signal transmission system 5 emits an RF pulse to the object 1 in order to cause nuclear magnetic resonance in the nuclear spins of atoms which form the body tissue of the object 1, and is configured to include a high frequency oscillator 11, a modulator 12, a high frequency amplifier 13, and a transmission-side high frequency coil (transmission coil) 14a. A high frequency pulse output from the high frequency oscillator 11 is amplitude-modulated by the modulator 12 at the timing based on the command from the sequencer 4, and the amplitude-modulated high frequency pulse is amplified by the high frequency amplifier 13 and is then supplied to the high frequency coil 14a disposed adjacent to the object 1. As a result, an RF pulse is emitted to the object 1.

The signal receiving system 6 detects an echo signal (NMR signal) emitted by nuclear magnetic resonance of the nuclear spins, which form the body tissue of the object 1, and is configured to include a receiving-side high frequency coil (receiving coil) 14b, a signal amplifier 15, a quadrature phase detector 16, and an A/D converter 17. The NMR signal of the response of the object 1 induced by the electromagnetic waves emitted from the transmission-side high frequency coil 14a is detected by the high frequency coil 14b disposed adjacent to the object 1 and amplified by the signal amplifier 15. Then, at the timing based on the command from the sequencer 4, it is divided into two signals perpendicular to each other by the quadrature phase detector 16, and each of them is converted into a digital amount by the A/D converter 17 and transmitted to the signal processing system 7.

The signal processing system 7 performs various kinds of data processing and performs display, storage, and the like of the processing results, and includes an external storage device such as an optical disc 19 and magnetic disk 18, an internal storage device such as a ROM 21 and a RAM 22, and a display 20 such as a CRT. When the data from the signal receiving system 6 is input to the CPU 8, the CPU 8 executes processing, such as signal processing and image reconstruction, and as a result displays a tomographic image of the object 1 on the display 20 and also records the tomographic image on the magnetic disk 18 or the like of the external storage device.

An operating section 25 inputs various kinds of control information regarding the MRI apparatus or control information regarding the processing performed in the signal processing system 7, and is configured to include a track ball or mouse 23 and a keyboard 24. This operating section 25 is disposed adjacent to the display 20, so that the operator controls various kinds of processing of the MRI apparatus interactively through the operating section 25 while observing the display 20.

Moreover, in FIG. 1, the transmission-side high frequency coil 14a and the gradient magnetic field coil 9 are provided in the static magnetic field space of the static magnetic field generation system 2, in which the object 1 is inserted, such that they face the object 1 in the case of a vertical magnetic field method and they surround the object 1 in the case of a horizontal magnetic field method. In addition, the receiving-side high frequency coil 14b is provided so as to face or surround a measurement part of the object 1, for example, the head.

Nuclides imaged by current MRI apparatuses, which are widely used clinically, have a hydrogen nucleus (proton) which is a main constituent material of the object. The shapes or functions of the head, abdomen, limbs, and the like of the human body are imaged in a two-dimensional or three-dimensional manner by imaging of the spatial distribution of proton density or the information regarding the spatial distribution of a relaxation time of an excited state.

Next, estimation of the SAR in the present invention will be described. The estimation of the SAR in the present invention is characterized in that the partial body SAR for a part of an object is estimated by calculating a signal generated from the part of the object and a signal generated from a wide region of the object including the part of the object, calculating the ratio between the signal generated from the part of the object and the signal generated from the entire wide region, and calculating the energy absorbed into the part of the object using the ratio of the signals.

First, it will be described that the partial body SAR for the part of the object can be estimated on the basis of the ratio between the signal generated from the part of the object and the signal generated from the entire wide region. Generally, the SAR is proportional to the square of the strength of a high frequency magnetic field $B_1$ (Expression 5).

[Expression 5]

$$SAR(\vec{r}) \propto |B_1(\vec{r})|^2 \qquad \text{(Expression 5)}$$

Here, since a high frequency magnetic field changes depending on the position, the SAR is described as a function of a position vector r.

As high frequency magnetic fields contributing to the SAR, there are $B_1^+$ which flips the spins and $B_1^-$ which cannot be observed in the MRI. The definition of $B_1^+$ and $B_1^-$ is given by (Expression 6) and (Expression 7), respectively. In addition, the relationship between the flip angle (FA) and the $B_1^+$ is shown in (Expression 8).

[Expression 6]

$$B_1^+(\vec{r}) \equiv \frac{B_{1x}(\vec{r}) + iB_{1y}(\vec{r})}{\sqrt{2}} \qquad \text{(Expression 6)}$$

-continued

[Expression 7]

$$\vec{B_1^-}(\vec{r}) \equiv \left\{ \frac{B_{1x}(\vec{r}) - iB_{1y}(\vec{r})}{\sqrt{2}} \right\}^* \quad \text{(Expression 7)}$$

[Expression 8]

$$FA(\vec{r}) = \gamma |B_1^+(\vec{r})| \Delta t \quad \text{(Expression 8)}$$

Here, γ indicates a gyromagnetic ratio, and Δt indicates a time for which a high frequency magnetic field is applied. In addition, * means a complex conjugate in (Expression 7).

The Z-direction distribution in $B_1^+$ and $B_1^-$ is the same. For this reason, the SAR of $B_1^+$ and the SAR of $B_1^-$ are the same distribution in the Z direction. From (Expression 5) and (Expression 8), it can also be seen that the SAR is proportional to the square of the flip angle (FA).

On the other hand, the MRI signal strength depends on T1 value, T2 value, FA, repetition time TR, and echo time TE, as expressed in (Expression 9).

[Expression 9]

$$\text{MRIsignal}(\vec{r}) = f(T1(\vec{r}), T2(\vec{r}), TR, TE, FA(\vec{r})) \quad \text{(Expression 9)}$$

Figure 2:
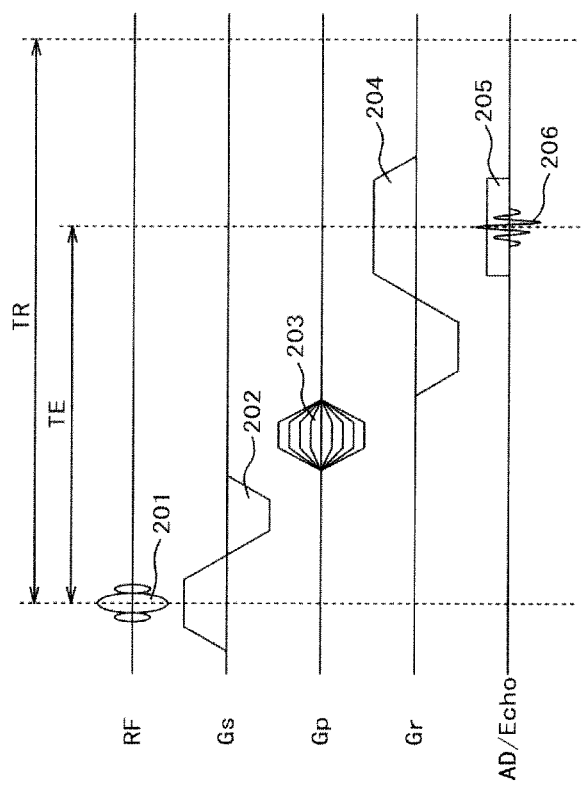
FIG. 2 is a Gradient Echo sequence diagram.
Figure 3:
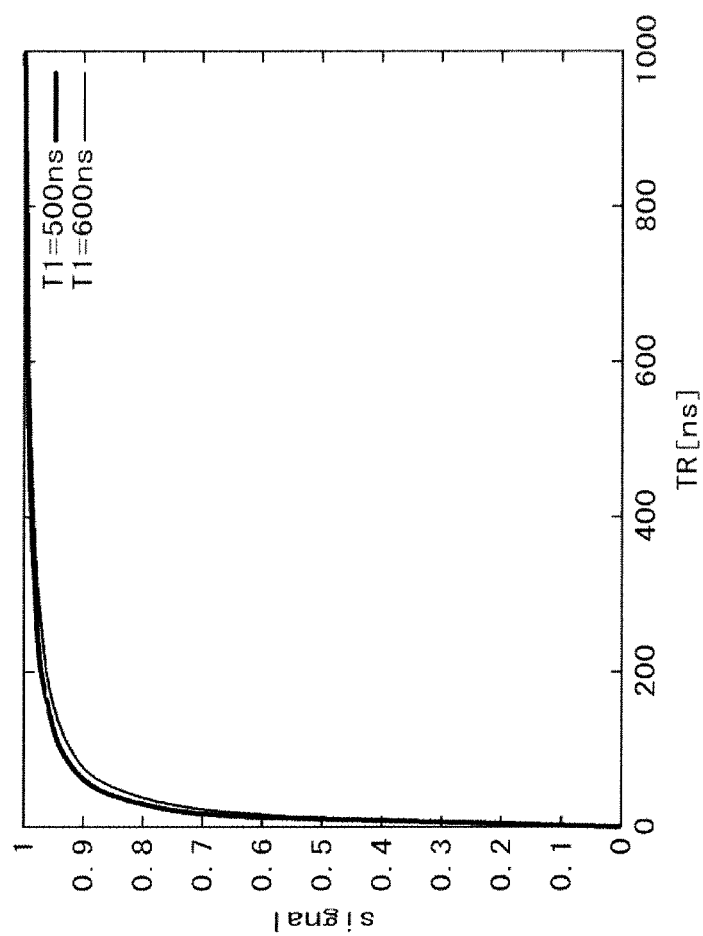
FIG. 3 is a conceptual diagram of T1 relaxation.
Figure 4:
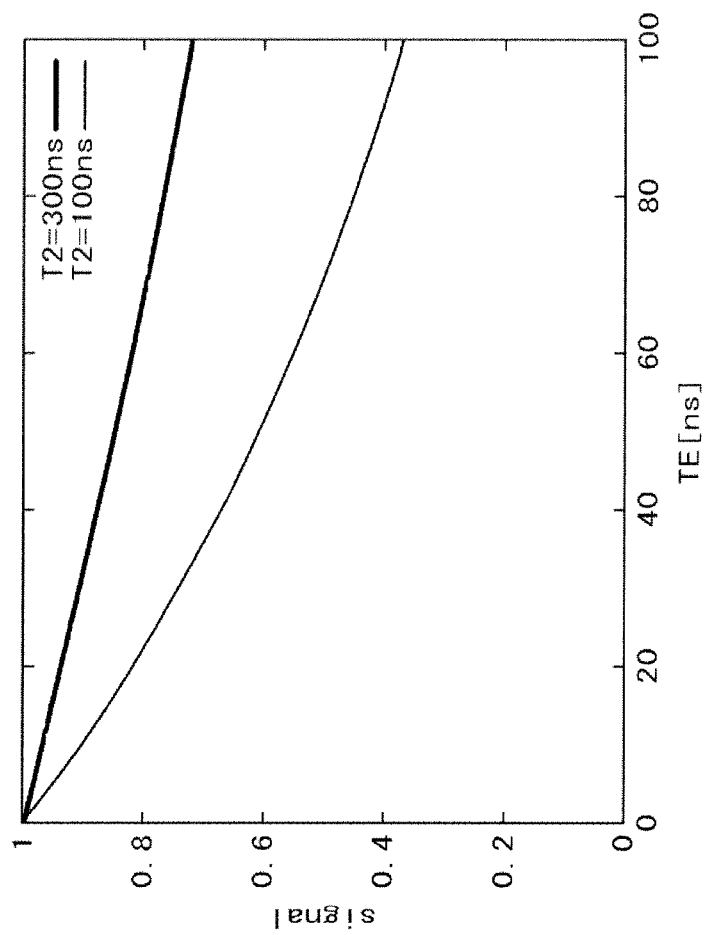
FIG. 4 is a conceptual diagram of T2 relaxation.

Here, f is a function determined by the imaging sequence. FIG. 2 shows a view in the Gradient Echo sequence as an example of the typical sequence, FIG. 3 shows a schematic view of T1 relaxation, and FIG. 4 shows a schematic view of T2 relaxation. In FIG. 2, 201 is an RF pulse, 202 is a slice selection gradient magnetic field pulse, 203 is a phase encoding gradient magnetic field pulse, 204 is a frequency encoding gradient magnetic field pulse, 205 is a sampling window, and 206 is an echo signal. By using the TR and the TE which are sufficiently small, it is possible to reduce the contribution of T1, T2, TR, and TE, and the MRI signal strength can be approximately set as a function of only FA (Expression 10).

[Expression 10]

$$\text{MRIsignal}(\vec{r}) = f(FA(\vec{r})) \quad \text{(Expression 10)}$$

That is, the FA can be calculated as an inverse function of an MRI signal (Expression 11).

[Expression 11]

$$FA(\vec{r}) = f^{-1}(\text{MRIsignal}(\vec{r})) \quad \text{(Expression 11)}$$

Using (Expression 5) and (Expression 8), the SAR can be calculated as a function of an MRI signal.

[Expression 12]

$$SAR(\vec{r}) \propto [f^{-1}(\text{MRIsignal}(\vec{r}))]^2 \quad \text{(Expression 12)}$$

Using the reference SAR measured using a reference RF pulse, the energy E absorbed into the whole object is calculated using the ratio between the reference RF pulse and a pulse actually used.

[Expression 13]

$$E[W] = Wc \times \frac{T_0}{T} \times \frac{S}{S_0} \times \left(\frac{FA}{FA_0}\right)^2 \quad \text{(Expression 13)}$$

Here, Wc is the amount of absorption of RF pulses measured using the reference RF pulse, $T_0$ is an application time of the reference RF pulse, $FA_0$ is the flip angle of the reference RF pulse, and $S_0$ is the amount obtained by integrating the square of the function, which is obtained by normalizing the waveform of the reference RF pulse to [0,1], from time t=0 to t=T. In addition, T indicates an application time of an RF pulse actually used, and S indicates the amount obtained by integrating the square of the function, which is obtained by normalizing the waveform of the RF pulse actually used to [0,1], from time t=0 to t=T. For measurement of Wc, the reference RF pulse is emitted to measure the energy of an incident wave and a reflected wave, and the power of the absorbed RF pulse is measured by taking the difference thereof. Since contribution of both $B_1^+$ and $B_1^-$ is included in Wc, contribution of both $B_1^+$ and $B_1^-$ is included in E. The whole body SAR can be calculated by dividing E by the mass M of the object.

Regarding (Expression 12), by calculating the ratio of the integral amount $S_b$ (Expression 14) over the entire region (wide region including the head region) covered by the receiving coil and the integral amount $S_h$ (Expression 14) of the head region (Expression 12), the ratio α of the energy absorbed into the head can be calculated (Expression 15). α is calculated by acquiring a signal using the same irradiation coil as an irradiation coil used in the main imaging sequence.

[Expression 14]

$$S_h = \int_{L_{head}} d\vec{r} \left[ f^{-1}(\text{MRIsignal}(\vec{r})) \right]^2 \quad \text{(Expression 14)}$$

$$S_b = \int_{L_{coil}} d\vec{r} \left[ f^{-1}(\text{MRIsignal}(\vec{r})) \right]^2$$

[Expression 15]

$$\alpha = \text{ratio of energy absorbed into the head} = \frac{S_h}{S_b} \quad \text{(Expression 15)}$$

Figure 16:
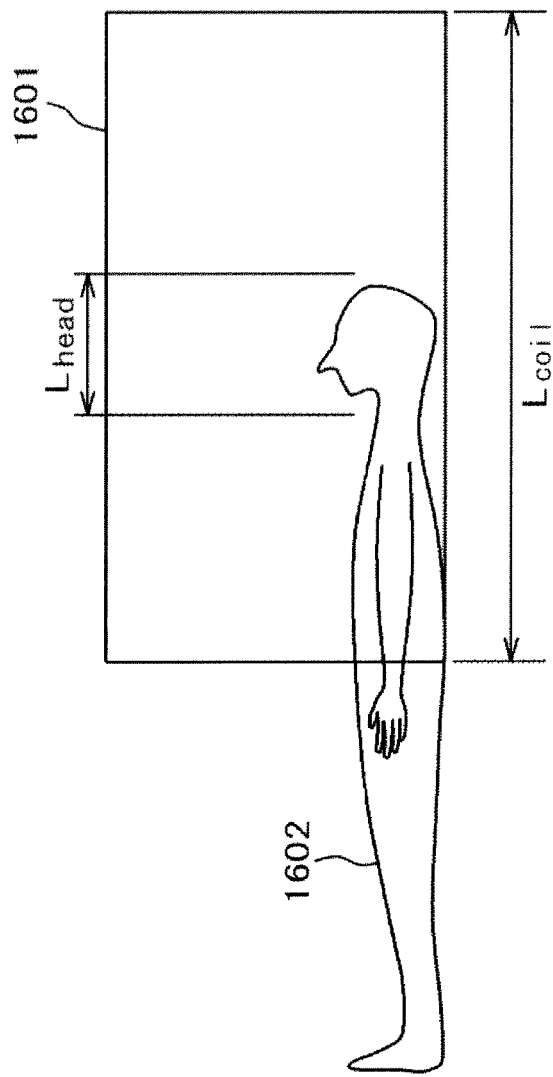
FIG. 16 is a view showing regions of a coil and the head.

Here, $L_{head}$, $L_{coil}$ in (Expression 14) indicate a head region and a region covered by the receiving coil which are defined in FIG. 16, respectively. By multiplying the energy E absorbed into the whole object by α, it is possible to calculate energy $E_h$ absorbed into the head.

[Expression 16]

$$E_h = \alpha E \quad \text{(Expression 16)}$$

The head SAR can be calculated by dividing $E_h$ by the mass of the head.

[Expression 17]

$$\text{Head } SAR = \frac{E_h}{m_h} \quad \text{(Expression 17)}$$

In addition, although the head SAR has been described above, the SAR of a part of the body may be estimated by acquiring a signal of an observed part of the body.

Hereinafter, each example regarding a method of calculating the ratio between a signal generated from a part of an object and a signal generated from the entire wide region of the object will be described in detail. In addition, in each of the following examples, the head is set as an example of a part of the object. However, other partial regions may be set without being limited to the head.

FIRST EXAMPLE

A first example of the present invention will be described. The first example is characterized in that the head SAR is calculated using the ratio between a signal, which is received from the entire transmission-reception RF coil (TR-body coil) that covers a wide region including the head, and a signal received from the head.

Figure 11:
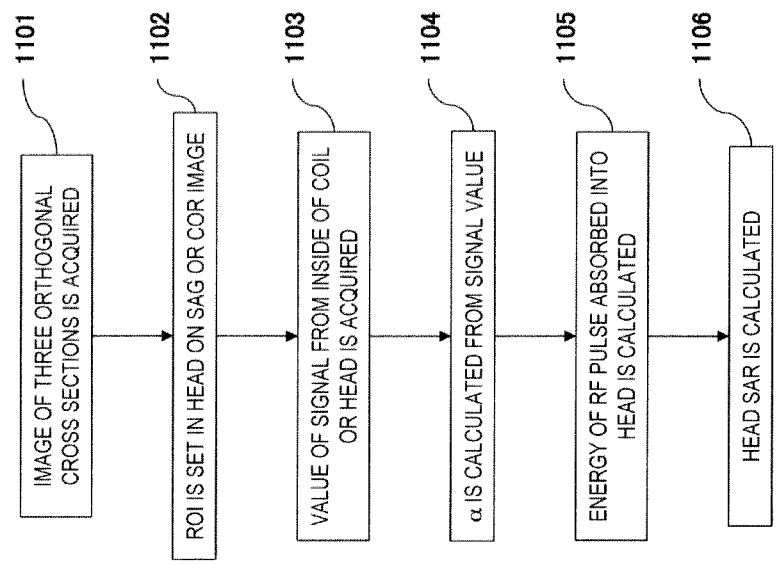
FIG. 11 is a flow chart of the first and second examples of the present invention.

An operation in the first example will be described using FIG. 11. FIG. 11 is a flow chart regarding the first example.

Details of Each Step are Shown Below.

Step 1101: An image of three orthogonal cross sections having the inside of the entire TR-body coil as an imaging field of view is acquired. As a sequence in this case, for example, the Gradient Echo expressed in the sequence diagram in FIG. 2 is used.

Figure 5:
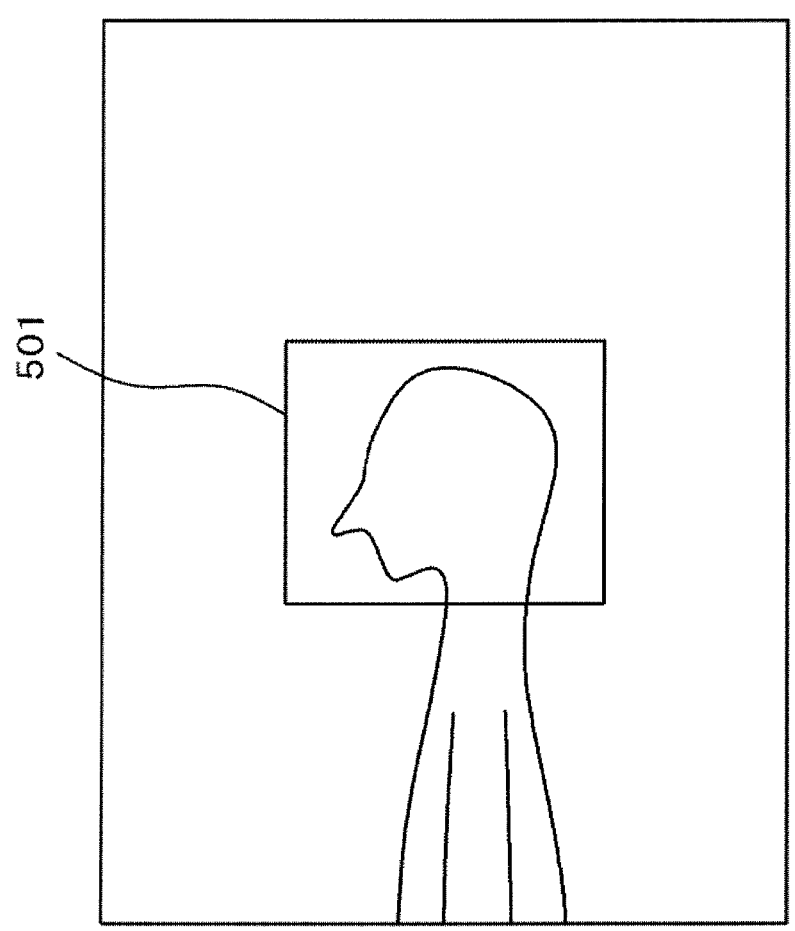
FIG. 5 is an example of a head ROI setting by an SAG image.
Figure 6:
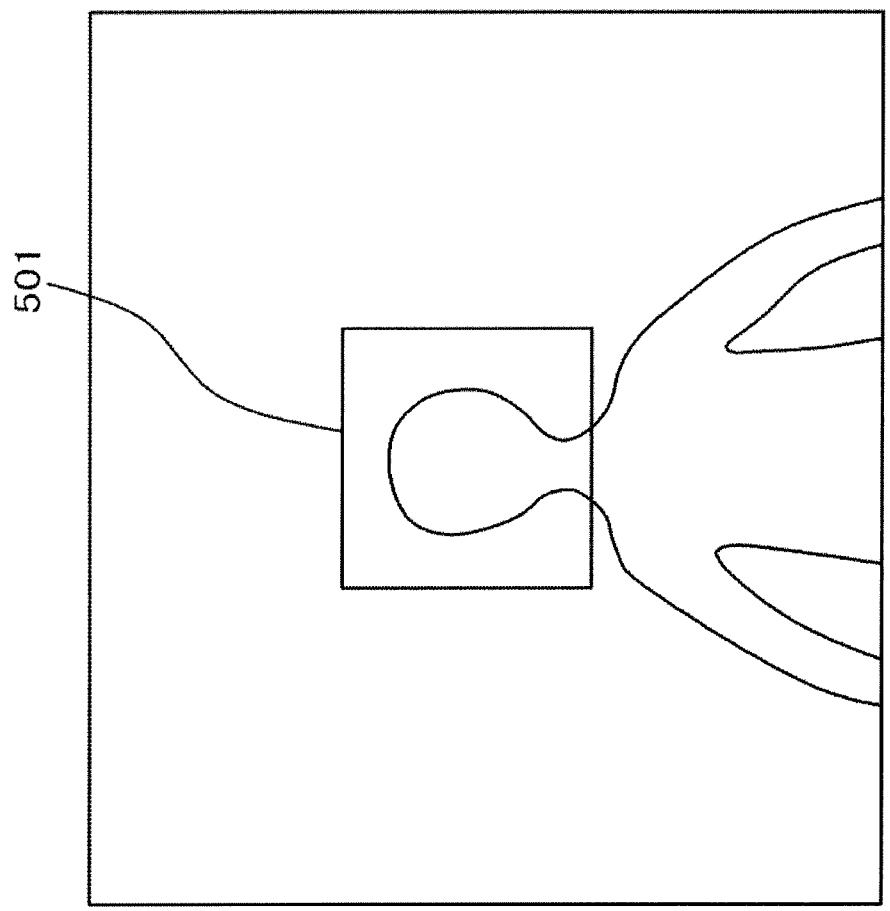
FIG. 6 is an example of a head ROI setting by a COR image.

Step 1102: An ROI is set in the head on the image acquired in step 1101. As the setting method, for example, as shown in FIG. 5 or 6, an ROI 501 is set in the head on an SAG image or a COR image.

Figure 7:
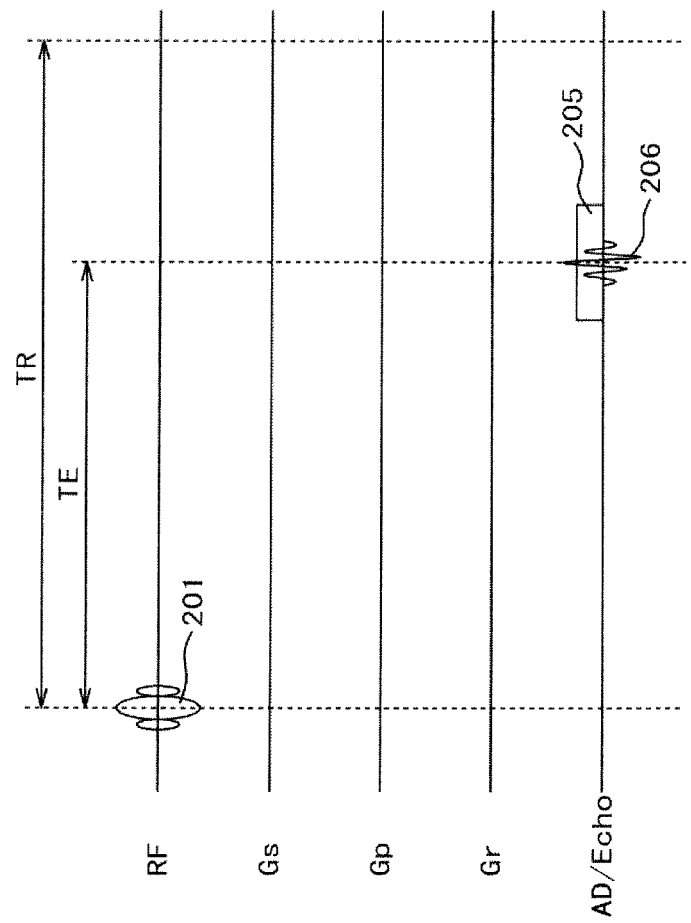
FIG. 7 is a sequence diagram for detecting an FID signal from the inside of the entire TR-body coil.
Figure 8:
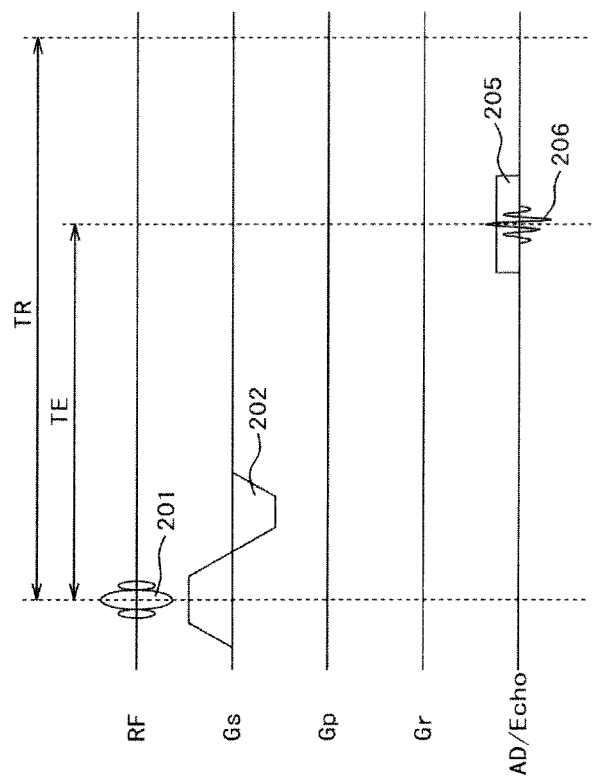
FIG. 8 is a sequence diagram for detecting an FID signal from the ROI of the head.

Step 1103: Using the sequence for SAR measurement, a signal $S_b$ (n) from the inside of the entire TR-body coil and a signal $S_h$ (n) from the head are acquired. As a sequence used at this time, a sequence which applies a slice selection gradient magnetic field pulse 202 to excite a region (head region) selected in the ROI is used for acquisition of the signal $S_h$ (n) from the head and a sequence which excites a wide region covered by the TR-body coil without applying a slice selection gradient magnetic field pulse is used for acquisition of the signal $S_b$ (n) from the inside of the entire TR-body coil, as shown in FIGS. 7 and 8, thereby acquiring an FID signal. Here, the FID signal is a free damping signal which appears after the application of a 90° pulse.

Step 1104: α given by (Expression 15) is calculated using $S_b$ (n) and $S_h$ (n) acquired in step 1103. Here, as a signal value used for calculation of α, an integral value of the signal which is acquired during AD of the window 205 and is given by (Expression 18) in the case of calculation using the FID signal is used.

[Expression 18]

$$S_h = \sum_{n=1}^{N} \{f^{-1}(S_h(n))\}^2 \qquad \text{(Expression 18)}$$

$$S_b = \sum_{n=1}^{N} \{f^{-1}(S_b(n))\}^2$$

Here, n is a number of the point sampled during AD, and 1≤n≤N. In this case, α is given by α=$S_h$/$S_b$. Step 1105: Energy absorbed into the head is calculated using (Expression 16). Step 1106: Head SAR is calculated using (Expression 17).

As described above, in the first example, an FID signal is acquired, and a signal generated from the head and a signal generated from the entire wide region are calculated from the FID signal. In addition, an image of the three orthogonal cross sections having the inside of the entire TR-body coil as an imaging field of view is acquired, and a head region is selected using the image of the three orthogonal cross sections. From the first example, it is possible to estimate the head SAR with high precision.

SECOND EXAMPLE

In this example, projection data in the body axis direction is used to calculate the ratio α.

Figure 9:
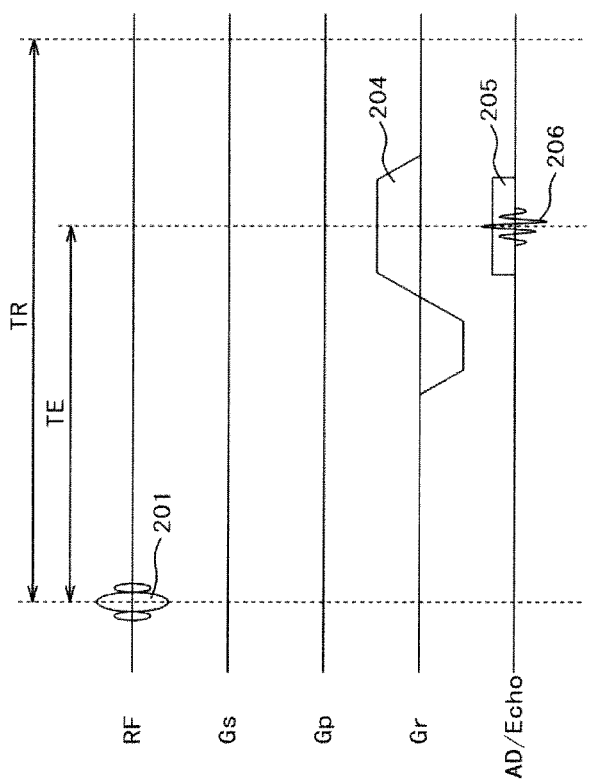
FIG. 9 is a sequence diagram for detecting an echo signal from the inside of the entire TR-body coil.
Figure 10:
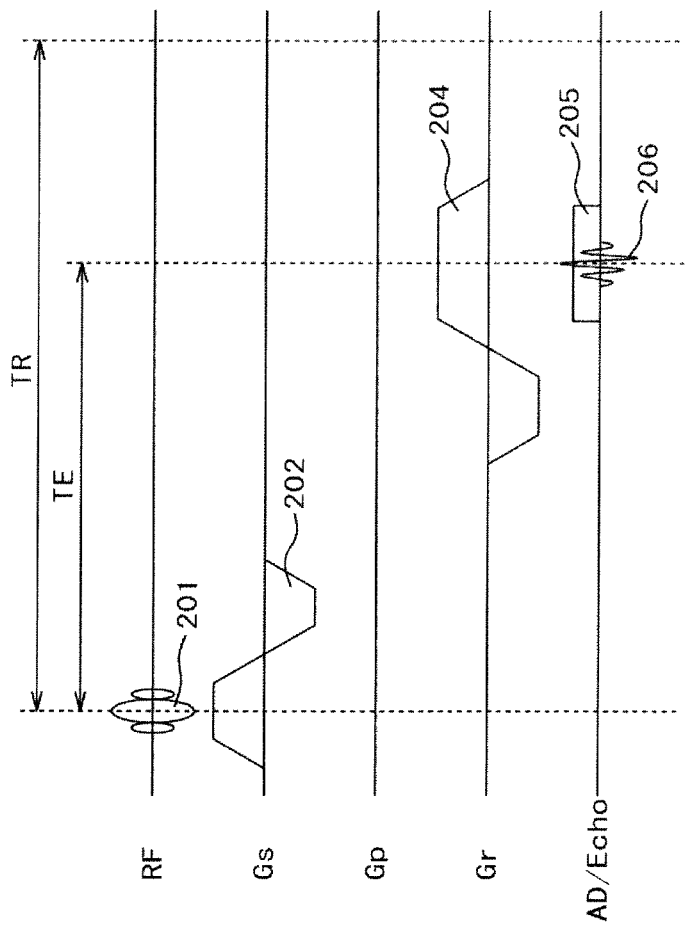
FIG. 10 is a sequence diagram for detecting an echo signal from the ROI of the head.

As shown in FIGS. 9 and 10, a sequence which applies a readout gradient magnetic field pulse 204 in the body axis direction is used as the sequence, which acquires $S_b$(n) and $S_h$(n) in step 1103 in the first example, in order to acquire an echo signal. In addition, a Fourier transform of the measured echo signal is performed to collect the projection data $P_b$(z) and $P_h$(z) in the body axis direction.

In step 1104, a spatial integral value of the projection data, which is given by (Expression 19), is used. Here, z indicates the position in the body axis direction.

[Expression 19]

$$S_h = \sum_{z=z_1}^{z=z_2} \{f^{-1}(P_h(z))\}^2 \qquad \text{(Expression 19)}$$

$$S_b = \sum_{z=-Z_1}^{z=Z_2} \{f^{-1}(P_b(z))\}^2$$

In this case, α is given by α=$S_h$/$S_b$.

As described above, in the second example, projection data in the body axis direction is acquired, and a signal generated from the head and a signal generated from the entire wide region are calculated from the projection data signal. From the second example, it is possible to estimate the head SAR with high precision.

THIRD EXAMPLE

Figure 12:
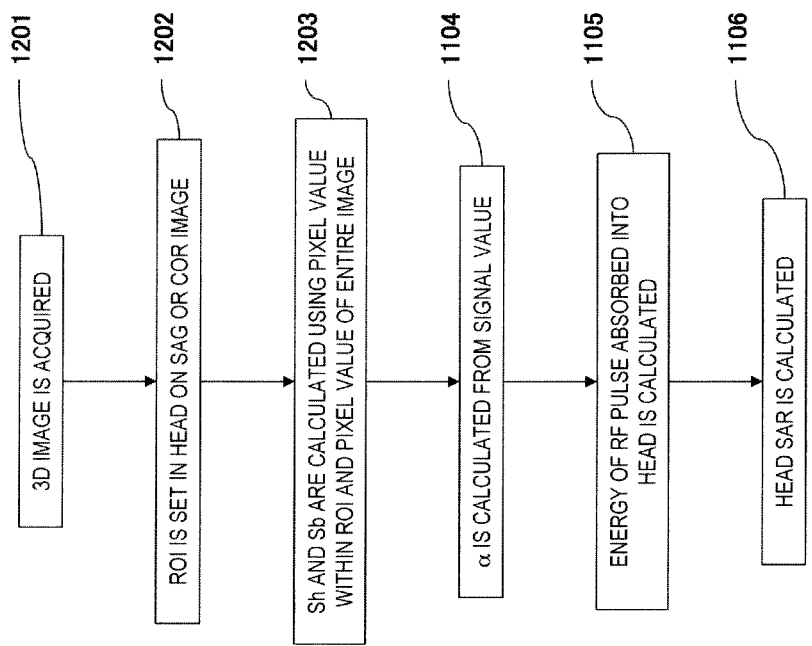
FIG. 12 is a flow chart of a third example of the present invention.

A third example of the present invention will be described using FIG. 12. FIG. 12 is a flow chart regarding the third example. Unlike the first example, the third example is characterized in that a 3D image is acquired and the head SAR is calculated from the image. Hereinafter, only different parts will be described, and explanation regarding the same parts will be omitted. Details of each step are shown below.

Figure 20:
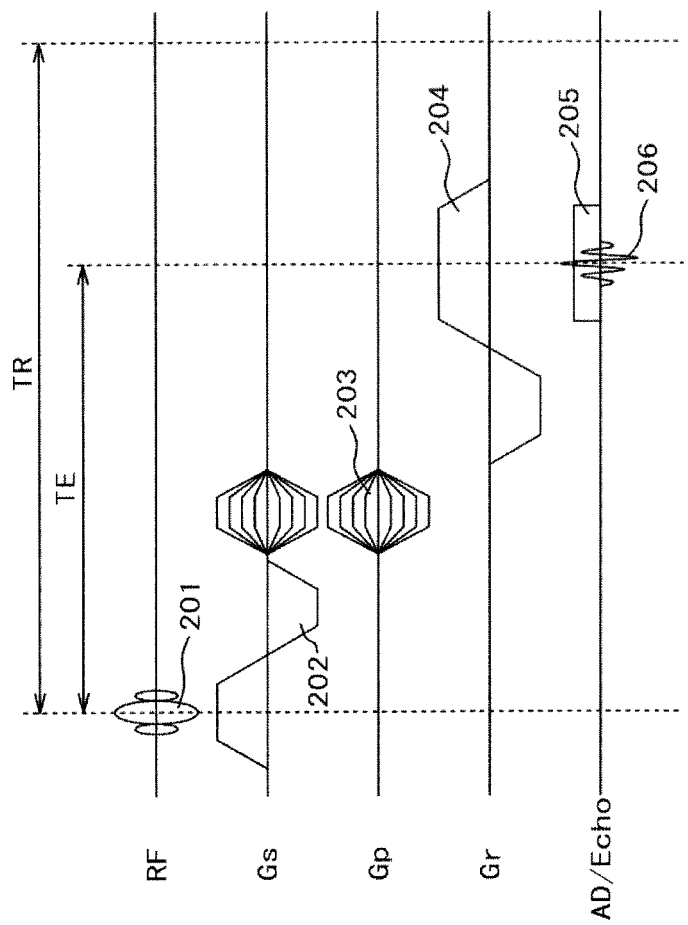
FIG. 20 is a 3D Gradient Echo sequence diagram.

Step 1201: A 3D image I (x, y, z) having the inside of the entire TR-body coil as an imaging field of view is captured. As a sequence in this case, for example, the 3D Gradient Echo expressed in the sequence diagram in FIG. 20 is used.

Step 1202: An ROI is set in the head. That is, a head region is selected as an ROI.

Figure 18:
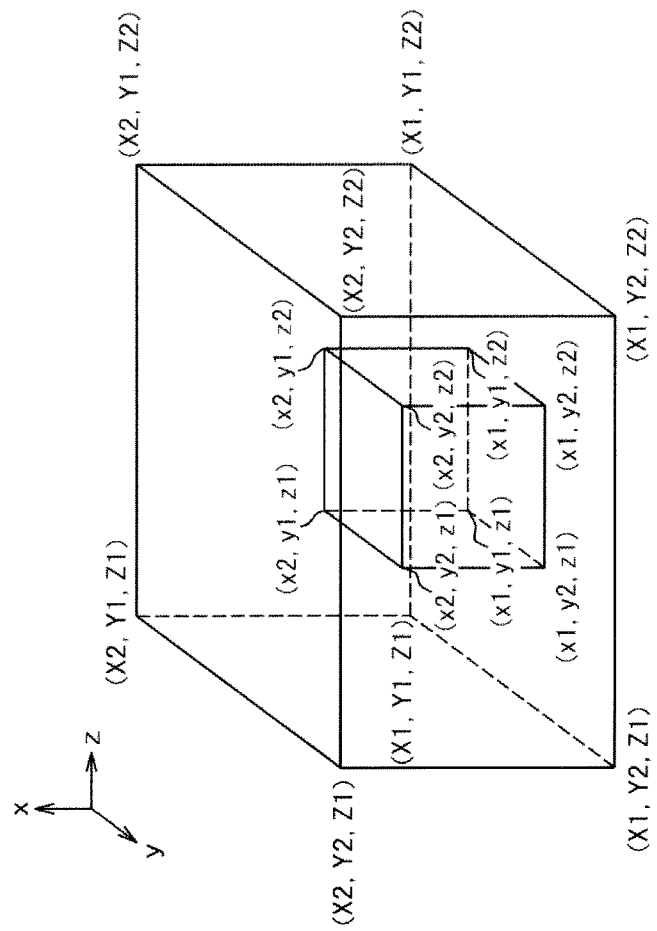
FIG. 18 is a view showing the coordinates of the head and the coordinates of the TR-body coil.

Step 1203: $S_h$ and $S_b$ are calculated using the pixel value in the ROI and the pixel value of the entire image. In this case, $S_h$ and $S_b$ are given by (Expression 20) . Here, as shown in FIG. 18, the head is set as a region surrounded by [x1 x2], [y1 y2], and [z1 z2], and the region covered by the TR-body coil is set as a region surrounded by [X1 X2], [Y1 Y2], and [Z1 Z2].

[Expression 20]

$$S_h = \sum_{x=x1}^{x=x2} \sum_{y=y1}^{y=y2} \sum_{z=z1}^{z=z2} \{f^{-1}(I(x, y, z))\}^2 \qquad \text{(Expression 20)}$$

$$S_b = \sum_{x=X1}^{x=X2} \sum_{y=Y1}^{y=Y2} \sum_{z=Z1}^{z=Z2} \{f^{-1}(I(x, y, z))\}^2$$

As described above, in the third example, a 3D image having the inside of the entire TR-body coil as an imaging field of view is captured, and a signal generated from the head and a signal generated from the entire wide region are calculated from the pixel value of the 3D image. In this case, a head region is selected using the 3D image. From the third example, it is possible to calculate the head SAR with high precision without performing the sequence for SAR measurement and the sequence for determining the imaging position separately.

FOURTH EXAMPLE

Figure 13:
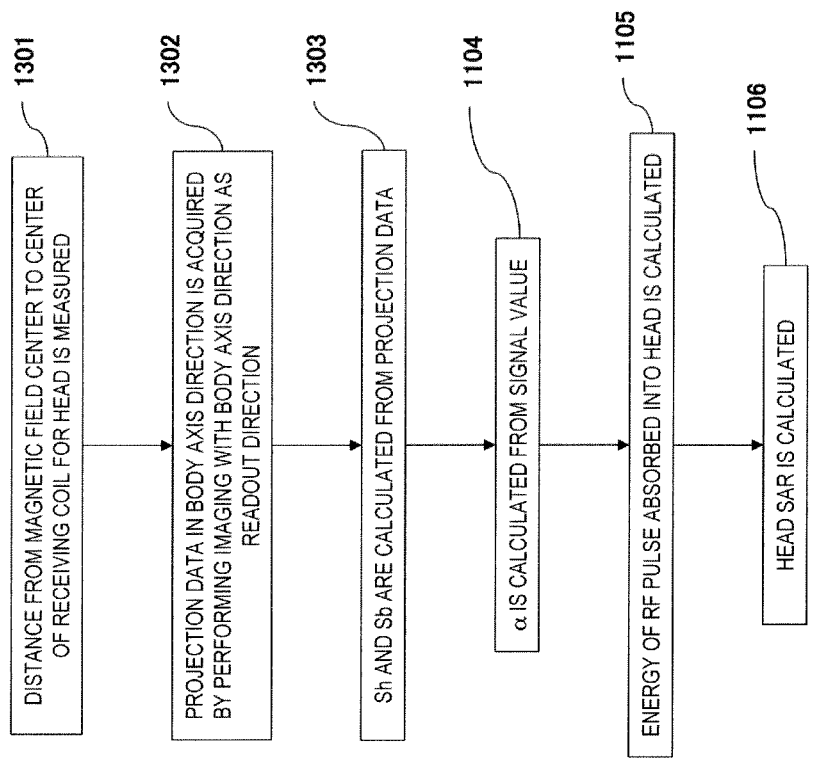
FIG. 13 is a flow chart of a fourth example of the present invention.

A fourth example will be described using FIG. 13. FIG. 13 is a flow chart regarding the fourth example. Unlike the first example, the fourth example is characterized in that calculation using the position of a receiving coil for the head is performed. Hereinafter, only different parts will be described, and explanation regarding the same parts will be omitted. Details of each step are shown below.

Step 1301: The position of the center of the receiving coil for the head is specified by a laser, and a distance I from the magnetic field center to the center of a receiving coil for the head 1701 is measured.

Figure 17:
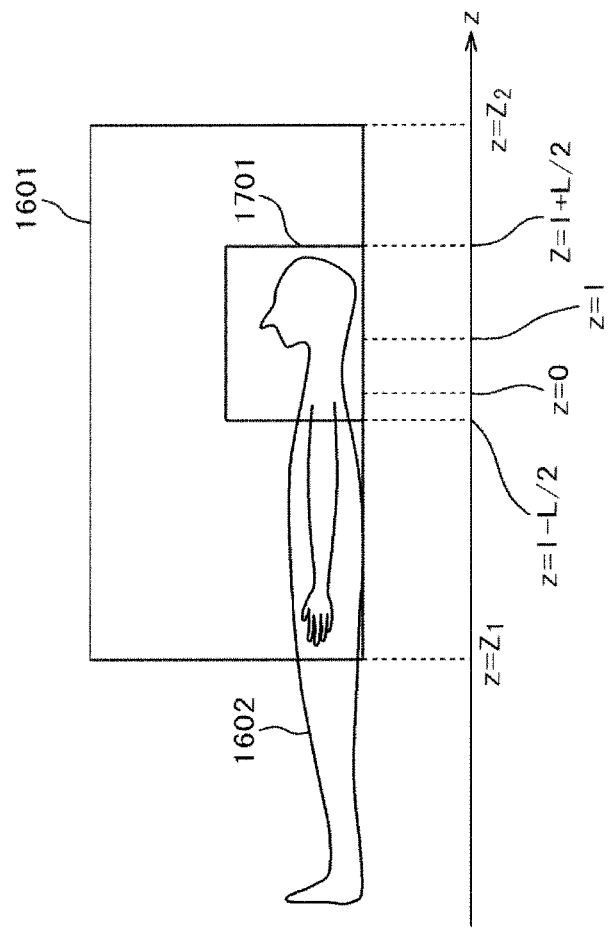
FIG. 17 is a view showing the coordinates of a head coil and a TR-body coil.

Step 1302: Imaging is performed with the inside of the entire TR-body coil as an imaging field of view. As a sequence in this case, for example, a sequence expressed in FIG. 9 is used. In FIG. 17, the z axis is a body axis direction, and the center of a TR-body coil 1601 is z=0. First, the readout gradient magnetic field pulse 204 is applied in the body axis direction in order to acquire projection data P(z) in the Z direction.

Step 1303: $S_h$ and $S_b$ are calculated from the projection data of a region of [I-L/2 I+L/2] of the receiving coil for head 1701 and the projection data of the entire region. $S_h$ and $S_b$ are given by (Expression 21). Here, L is the length of the receiving coil for head 1701 in the z direction.

[Expression 21]

$$S_h = \sum_{z=I-L/2}^{z=I+L/2} \{f^{-1}(P(z))\}^2 \quad \text{(Expression 21)}$$

$$S_b = \sum_{z=Z_1}^{z=Z_2} \{f^{-1}(P(z))\}^2$$

As described above, in the fourth example, the position of the receiving coil for the head is measured, and a head region is selected using the position of the receiving coil for the head. From the fourth example, it is possible to calculate the head SAR with high precision by extracting a region of the head automatically.

FIFTH EXAMPLE

Figure 14:
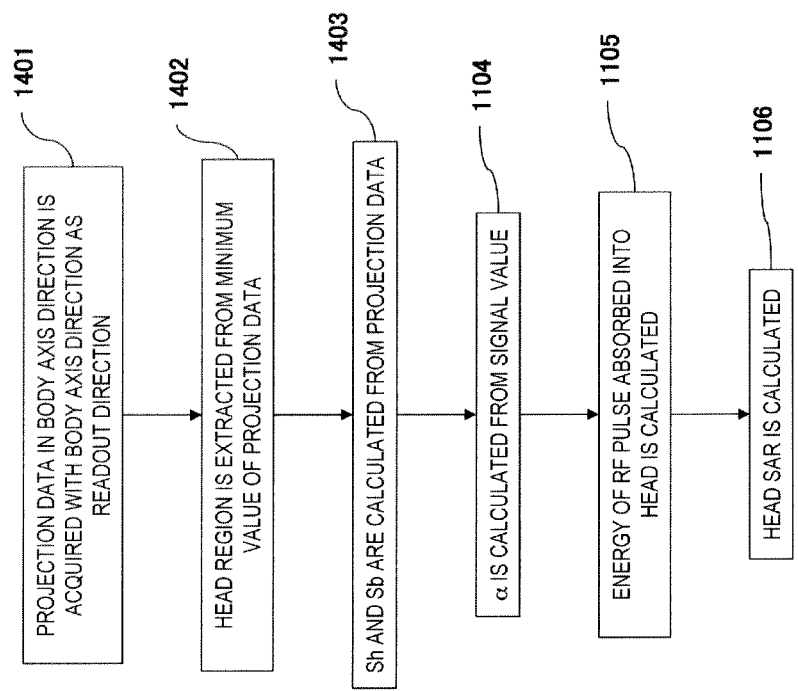
FIG. 14 is a flow chart of a fifth example of the present invention.

Next, a fifth example will be described using FIG. 14. FIG. 14 is a flow chart regarding the fifth example. The fifth example is different from the first example and the like in that a region of the head is extracted using the minimum value of the projection data in the body axis direction. Hereinafter, only different parts will be described, and explanation regarding the same parts will be omitted. Details of each step are shown below.

Step 1401: A readout gradient magnetic field is applied in the body axis direction and imaging is performed with the inside of the entire TR-body coil as an imaging region in order to acquire the projection data of a signal in the body axis direction. As a sequence in this case, for example, a sequence expressed in FIG. 9 is used.

Figure 19:
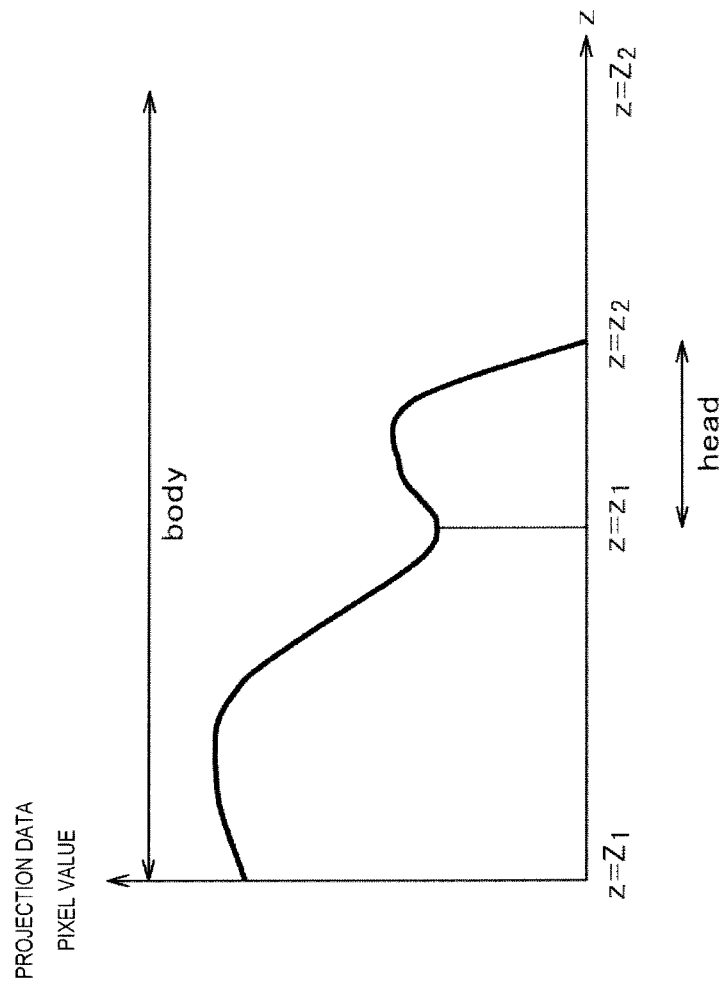
FIG. 19 is a conceptual diagram of projection data.

Step 1402: With the acquired projection data, a portion corresponding to the head can be distinguished since a signal in the portion is small compared with signals in portions other than the head. As a distinction method, for example, it is distinguished at the point $z_1$ where the pixel value of the projection data P(z) is a minimum value as shown in FIG. 19.

Step 1403: $S_h$ and $S_b$ defined by (Expression 14) are given by (Expression 22). Here, the entire region covered by the TR-body coil is set as [Z1, Z2], and the head region is set as [z1, z2].

[Expression 22]

$$S_h = \sum_{z=z_1}^{z=z_2} \{f^{-1}(P_h(z))\}^2 \quad \text{(Expression 22)}$$

$$S_b = \sum_{z=-Z_1}^{z=Z_2} \{f^{-1}(P_b(z))\}^2$$

α in (Expression 15) is given by $\alpha = S_h/S_b$.

As described above, in the fifth example, the projection data in the body axis direction is acquired, and a head region is selected from the minimum value of the projection data. From the fifth example, it is possible to calculate the head SAR with high precision by extracting a region of the head automatically.

SIXTH EXAMPLE

Next, a sixth example will be described. The sixth example is different from the first example and the like in that the FA is directly calculated by measuring B1map without using an inverse function of the signal strength. The B1map indicates the distribution of the strength and phase in an imaging region of emitted RF pulses. The B1map is used in RF shimming for correcting the non-uniformity of emission of an RF pulse in the imaging region. As a method of creating the B1map, it is possible to use the method disclosed in NPL 3, for example. However, the method of creating the B1map is not limited in the present invention, and any creation method may be used. Since the B1map is a complex number, the absolute value becomes FA. The square of the absolute value is calculated by integration for a head region (head) and the entire wide region (whole body), and the ratio a of these integral values is calculated. That is, the ratio a is given by Expression 23.

[Expression 23]

$$\alpha = \frac{\int_{head} d\vec{r} \left[FA(\vec{r})\right]^2}{\int_{whole\ body} d\vec{r} \left[FA(\vec{r})\right]^2} \quad \text{(Expression 23)}$$

In this Expression 23, the FA indicates the value of the B1map. However, the FA may also be a relative value to a certain reference value (for example, a maximum value of the FA). However, in the case of the relative value, the reference value is set to be equal in the numerator and the denominator. In addition, [ ] means taking the absolute value of a complex number thereinside.

As described above, in the sixth example, a signal generated from the head and a signal generated from the whole object are calculated using the B1map. From the sixth example, it is possible to estimate the head SAR with high precision using the B1map (distribution of B1).

(Common Flow)

Figure 15:
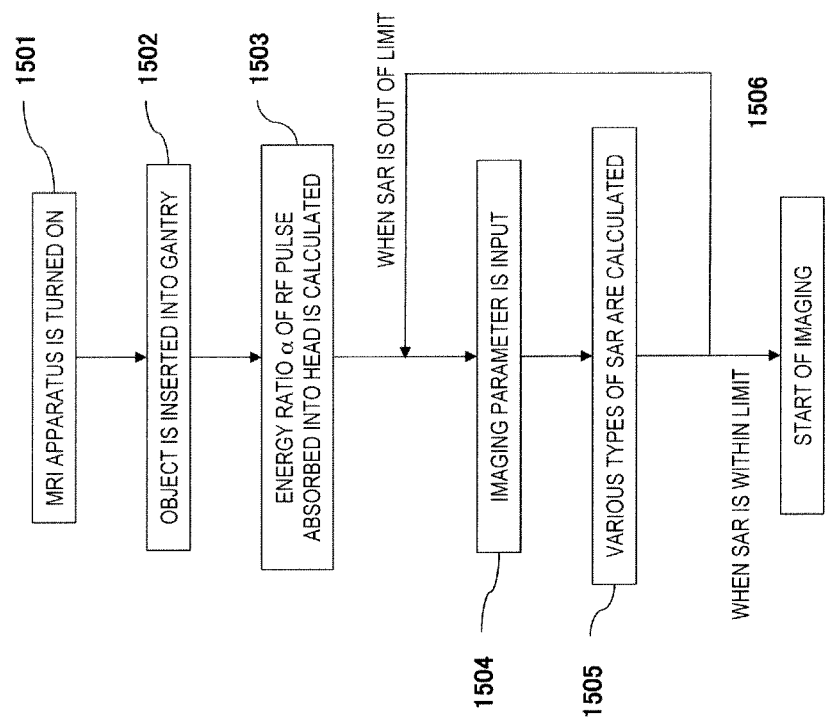
FIG. 15 is a common workflow in the first to sixth examples.

A common workflow in the first to sixth examples described above will be described using FIG. 15. Details of each step are shown below.

Step 1501: An MRI operator turns on the MRI apparatus.

Step 1502: The MRI operator sets an object on a table and inserts the table into the gantry.

Step 1503: The MRI apparatus measures a defined by (Expression 15) using the method in each example.

Step 1504: The MRI operator inputs an imaging parameter and object information.

Step 1505: The MRI apparatus calculates the whole body SAR, the partial body SAR, and the head SAR using the input imaging parameter and object information. The MRI apparatus compares the calculated SAR with the SAR limit value and returns to the imaging parameter input when the SAR exceeds the SAR limit value.

Step 1506: When the SAR does not exceed the SAR limit value, the MRI apparatus starts imaging.

In addition, the first to third examples are examples of calculating the ratio α of the energy absorbed into the head, and the fourth and fifth examples are examples of calculating the position of the head. These may be executed in combination.

As described above, according to these examples, it is possible to calculate the head SAR accurately.

DESCRIPTION OF REFERENCE NUMERALS AND SIGNS

1: object
2: static magnetic field generation system
3: gradient magnetic field generation system
4: sequencer
5: signal transmission system
6: signal receiving system
7: signal processing system
8: central processing unit (CPU)
9: gradient magnetic field coil
10: gradient magnetic field power source
11: high frequency oscillator
12: modulator
13: high frequency amplifier
14a: high frequency coil (transmission coil)
14b: high frequency coil (receiving coil)
15: signal amplifier
16: quadrature phase detector
17: A/D converter
18: magnetic disk
19: optical disc
20: display
21: ROM
22: RAM
23: track ball or mouse
24: keyboard
201: RF pulse
202: slice selection gradient magnetic field pulse
203: phase encoding gradient magnetic field pulse
204: frequency encoding gradient magnetic field pulse
205: sampling window
206: echo signal
501: head ROI
1601: TR-body coil
1602: object
1701: receiving coil for head

The invention claimed is:

1. A nuclear magnetic resonance imaging apparatus comprising:
a static magnetic field generator configured to generate a static magnetic field in a space where an object is placed;
a gradient magnetic field application section configured to apply a gradient magnetic field to the object;
a high frequency magnetic field generator configured to apply an RF pulse with a magnetic resonance frequency to the object;
a signal detector configured to detect an echo signal generated from the object;
an image reconstruction section configured to reconstruct an image using the detected echo signal; and
a controller configured to control the gradient magnetic field application section, the high frequency magnetic field generator, and the signal detector,
wherein the controller estimates a partial body SAR regarding a part of the object by calculating an amount of the echo signal received by the signal detector and generated from the part of the object expressed by (14a) below and calculating an amount of the echo signal received by the signal detector and generated from a wide region of the object including the part of the object expressed by (14a) below, $$S_h = \int_{L_{head}} d\vec{r} [f^{-1}(MRIsignal(\vec{r}))]^2 \quad (14a)$$

$$S_b = \int_{L_{coil}} d\vec{r} [f^{-1}(MRIsignal(\vec{r}))]^2 \quad (14b)$$

calculating a ratio between the signal generated from the part of the object and the signal generated from the entire wide region expressed by $\alpha=S_h/S_b$, and calculating energy absorbed into the part of the object using the ratio of the signals, wherein a head region is defined by $L_{head}$, and $\vec{r}$ is a position vector, $f^{-1}$ is a function determined by an imaging function, MRIsignal ($\vec{r}$) is an MRI signal strength of $\vec{r}$.

2. The nuclear magnetic resonance imaging apparatus according to claim 1,
wherein the part of the object is a head of the object.

3. The nuclear magnetic resonance imaging apparatus according to claim 2,
wherein the controller is configured to acquire an FID signal and is configured to calculate a signal, which is generated from the head, and a signal, which is generated from the entire wide region, from the FID signal.

4. The nuclear magnetic resonance imaging apparatus according to claim 2,
wherein the controller is configured to acquire projection data in a body axis direction and is configured to calculate a signal, which is generated from the head, and a signal, which is generated from the entire wide region, from the projection data signal.

5. The nuclear magnetic resonance imaging apparatus according to claim 2,
wherein the controller is configured to capture a 3D image with the inside of an entire TR-body coil as an imaging field of view and is configured to calculate a signal, which is generated from the head, and a signal, which is generated from the entire wide region, from a pixel value of the 3D image.

6. The nuclear magnetic resonance imaging apparatus according to claim 2,
wherein the controller is configured to calculate a signal, which is generated from the head, and a signal, which is generated from the whole object, from a B1map.

* * * * *